(12) United States Patent
Atala et al.

(10) Patent No.: US 11,732,241 B2
(45) Date of Patent: Aug. 22, 2023

(54) METHODS OF PRODUCING IN VITRO LIVER CONSTRUCTS AND USES THEREOF

(71) Applicant: Wake Forest University Health Sciences, Winston-Salem, NC (US)

(72) Inventors: Anthony Atala, Winston-Salem, NC (US); Colin Bishop, Clemmons, NC (US); Ivy Mead, Inman, KS (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 364 days.

(21) Appl. No.: 15/768,293

(22) PCT Filed: Oct. 14, 2016

(86) PCT No.: PCT/US2016/056942
§ 371 (c)(1),
(2) Date: Apr. 13, 2018

(87) PCT Pub. No.: WO2017/070007
PCT Pub. Date: Apr. 27, 2017

(65) Prior Publication Data
US 2018/0320141 A1 Nov. 8, 2018

Related U.S. Application Data

(60) Provisional application No. 62/241,966, filed on Oct. 15, 2015.

(51) Int. Cl.
| | |
|---|---|
| *C12N 5/071* | (2010.01) |
| *C12M 3/00* | (2006.01) |
| *G01N 33/50* | (2006.01) |
| *B33Y 10/00* | (2015.01) |

(52) U.S. Cl.
CPC ............ *C12N 5/0671* (2013.01); *B33Y 10/00* (2014.12); *C12M 21/08* (2013.01); *C12N 5/067* (2013.01); *G01N 33/5088* (2013.01); *C12N 2502/14* (2013.01); *C12N 2503/02* (2013.01)

(58) Field of Classification Search
CPC .. C12N 5/0671; C12N 2502/14; C12N 5/067; C12N 2503/02; C12M 21/08
See application file for complete search history.

(56) References Cited

U.S. PATENT DOCUMENTS

| | | | |
|---|---|---|---|
| 5,624,840 A | 4/1997 | Naughton et al. | |
| 6,133,030 A * | 10/2000 | Bhatia | B82Y 30/00 435/177 |
| 6,197,575 B1 * | 3/2001 | Griffith | B01J 19/0046 435/288.4 |
| 6,737,270 B1 | 5/2004 | Michalopoulos et al. | |
| 2004/0110289 A1 | 6/2004 | Ludlow et al. | |
| 2010/0086936 A1 | 4/2010 | Sherley et al. | |
| 2011/0014126 A1 | 1/2011 | Evans et al. | |
| 2013/0189327 A1 | 7/2013 | Ortega et al. | |
| 2013/0323708 A1 | 12/2013 | Yarmush et al. | |
| 2014/0274802 A1 * | 9/2014 | Shepherd | G01N 33/5008 506/14 |
| 2014/0287960 A1 | 9/2014 | Shepherd et al. | |
| 2016/0168536 A1 | 6/2016 | Guillouzo | |

FOREIGN PATENT DOCUMENTS

| | | |
|---|---|---|
| JP | 2013532966 A | 8/2013 |
| WO | 2012014076 A2 | 2/2012 |
| WO | 2013190013 A1 | 12/2013 |
| WO | 2014151921 A1 | 9/2014 |
| WO | 2015005614 A1 | 1/2015 |
| WO | WO2015004482 A2 * | 1/2015 ............... C12N 7/00 |

OTHER PUBLICATIONS

Glaser et al. Cholangiocyte proliferation and liver fibrosis. Expert Rev Mol Med. Feb. 25, 2009, p. 1-22 (Year: 2009).*
Kmiec. Cooperation of Liver Cells in Health and Disease. Advances in anatomy, embryology and cell biology. vol. 161. p. 1-151 (Year: 1952).*
Maroni et al. Functional and Structural Features of Cholangiocytes in Health and Disease. Cell Mol Gastroenterol Hepatol 2015;1:368-380 (Year: 2015).*
Poisson et al. Liver sinusoidal endothelial cells: Physiology and role in liver diseases. Journal of Hepatology 2017 vol. 66: p. 212-227 (Year: 2017).*
Wong et al. Concave microwell based size-controllable hepatosphere as a three-dimensional liver tissue model. Biomaterials 32 (2011) 8087-8096 (Year: 2011).*
Usta et al. Microengineered cell and tissue systems for drug screening and toxicology applications: Evolution of in-vitro liver technologies. Technology (Singap World Sci). Mar. 2015 ; 3(1): 1-26. (Year: 2015).*
Gevaert et al. High Throughput Micro-Well Generation of Hepatocyte Micro-Aggregates for Tissue Engineering. PLoS One 9(8):e105171, p. 1-9 (Year: 2014).*
Soto-Guiterrez et al. Engineering of an Hepatic Organoid to Develop Liver Assist Devices. Cell Transplant. 2010 ; 19(6): 815-822 (Year: 2010).*
Extended European Search Report corresponding to European Patent Application No. 16858018.1 (10 Pages) (dated Feb. 22, 2019).
Kostadinova et al. "A long-term three dimensional liver co-culture system for improved prediction of clinically relevant drug-induced hepatotoxicity" Toxicology and Applied Pharmacology 268(1):1-16 (Jan. 23, 2013).
Michalopoulos et al. "Histological Organization in Hepatocyte Organoid Cultures" American Journal of Pathology 159(5):1877-1887 (Nov. 2001).

(Continued)

*Primary Examiner* — Taeyoon Kim
(74) *Attorney, Agent, or Firm* — Myers Bigel, P.A.

(57) ABSTRACT

Provided herein are cell compositions useful for making artificial liver constructs. The cell composition my include, in combination, (a) hepatocyte cells, (b) Kuppfer cells, (c) hepatic stellate cells, (d) sinusoidal endothelial cells, and (e) cholangiocyte cells.

24 Claims, 7 Drawing Sheets

(56) References Cited

OTHER PUBLICATIONS

Cavnar et al. "Transfer, Imaging, and Analysis Plate for Facile Handling of 384 Hanging Drop 3D Tissue Spheroids" Journal of Laboratory Automation 19(2):208-214 (2014).
Gunness et al. "3D Organotypic Cultures of Human HepaRG Cells: A Tool for In Vitro Toxicity Studies" Toxicological Sciences 133(1):67-78 (2013).
Kim et al. "3D Hepatic Cultures Simultaneously Maintain Primary Hepatocyte and Liver Sinusoidal Endothelial Cell Phenotypes" Public Library of Science One 5(11):e15456 (2010).
Messner et al. "Multi-cell type human liver microtissues for hepatotoxicity testing" Archives of Toxicology 87:209-213 (2013).
Si-Tayeb et al. "Organogenesis and Development of the Liver" Developmental Cell Review 18(2):175-189 (Feb. 16, 2010).
International Search Report and Written Opinion of the International Searching Authority corresponding to International Patent Application No. PCT/US2016/056942 dated Apr. 21, 2017. (8 pages).
Van De Bovenkamp M et al. Liver fibrosis in vitro: cell culture models and precision-cut liver slices. Toxicology in Vitro. 2007; 21: 545-557.
Handa K et al. Assembly of human organs from stem cells to study liver disease. The American Journal of Pathology. Feb. 2014; 184(2): 348-357.
Kaur S et al. Hepatic progenitor cells in action—liver regeneration or fibrosis? The American Journal of Pathology, Sep. 2015; 185(9): 2342-2350.
Ahsan MH et al. Kinetics of liver macrophages (Kupffer cells) in SIV-infected macaques. Virology. 2013; 446: 77-85.
Edmondson R et al. Three-dimensional cell culture systems and their applications in drug discovery and cell-based biosensors. Assay and Drug Development Technologies. May 2014; 12(4): 207-218.
Faulk DM et al. Decellularization and cell seeding of whole liver biologic scaffolds composed of extracellular matrix. Journal of Clinical and Experimental Hepatology. Mar. 2015; 5(1): 69-80.
International Search Report and Written Opinion, PCT/US2017/017158, dated Apr. 13, 2017, 9 pages.
International Preliminary Report on Patentability, PCT/US2017/017158, dated Aug. 14, 2018, 7 pages.
European Examination Report corresponding to EP 16858018.1; dated Jul. 20, 2020 (7 pages).
Japanese Office Action corresponding to JP 2018-519364; dated Sep. 1, 2020 (14 pages, including English translation).
Skardal, Aleksander, et al., "A hydrogel bioink toolkit for mimicking native tissue biochemical and mechanical properties in bioprinted tissue constructs", Acta Biomaterialia, 25, 2015, 24-34.
Lee, Jung Seung, et al., "Liver Extracellular Matrix Providing Dual Function of Two-Dimensional Substrate Coating and Three-Dimensional Injectable Hydrogel Platform for Liver Tissue Engineering", Biomacromolecules, 15(1), 2014, 206-218.
Australian Examination Report No. 1 corresponding to AU 2016340819; dated Aug. 18, 2022 (5 pages).
Canadian Office Action corresponding to CA 3,001,341; dated Oct. 26, 2022 (6 pages).
Canadian Office Action corresponding to CA 3,013,630; dated Feb. 22, 2023 (5 pages).
Japanese Office Action corresponding to JP2018-541608; dated Sep. 3, 2021 (5 pages, including English translation).
Australian Examination Report No. 1 for standard patent application, corresponding to AU 2017217688; dated Jul. 26 2022 (6 pages).
Extended Search Report corresponding to European Patent Application No. 17750748.0, dated Jul. 25, 2019, 10 pages.
Japanese Office Action in Corresponding to JP 2018-541608, dated Nov. 5, 2020, 9 pages.
Atta, Hussein, et al., "Mutant MMP-9 and HGF gene transfer enhance resolution of CCl4-induced liver fibrosis in rats: role of ASH1 and EZH2 methyltransferases repression", PLoS ONE 9(11): e112384, 2014, 1-11.
Baptista, Pedro, et al., "The use of whole organ decellularization for the generation of a vascularized liver organoid", Hepatology, 53(2), 2011, 604-617.
Deng, Xing, et al., "Hepatic stellate cells modulate the differentiation of bone marrow mesenchymal stem cells into hepatocyte-like cells", Journal of Cellular Physiology, 217(1), 2008, 138-144.
Eming, Sabine A., et al., "Wound repair and regeneration: mechanisms, signaling, and translation", Science Translational Medicine, 6(265), 2014, 1-16.
Kidd, Shannon, et al., "Origins of the tumor microenvironment: Quantitative assessment of adipose-derived and bone marrow-derived stroma", Plos ONE, 7(2): e30563, 2012, 1-12.
Klingberg, Franco, et al., "The myofibroblast matrix: implications for tissue repair and fibrosis", The Journal of Pathology, 229(2), 2013, 298-309.
Lang, Ren, et al., "Three-dimensional culture of hepatocytes on porcine liver tissue-derived extracellular matrix", Biomaterials, 32, 2011, 7042-7052.
Liedtke, Christian, et al., "Experimental liver fibrosis research: update on animal models, legal issues and translational aspects", Fibrogenesis & Tissue Repair, 6(1), 2013, 1-25.
Mann, Jelena, et al., "MeCP2 controls an epigenetic pathway that promotes myofibroblast transdifferentiation and fibrosis", Gastroenterology, 138(2), 2010, 705-714.
Mazza, et al., "Decellularized human liver as a natural 3D-scaffold for liver bioengeneering and transplantation", Scientific Reports, vol. 5, 2015, 1-5.
Mitaka, Toshihiro, et al., "Reconstruction of hepatic organoid by hepatic stem cells", Journal of Hepato-Biliary-Pancreatic Surgery, 9(6), 2002, 697-703.
Miyajima, Atsushi, et al., "Stem/progenitor cells in liver development, homeostasis, regeneration, and reprogramming", Cell Stem Cell, 14(5), 2014, 561-574.
Spaeth, Erika L., et al., "Mesenchymal CD44 expression contributes to the acquisition of an activated fibroblast phenotype via TWIST activation in the tumor microenvironment", Cancer Research, 73(17), 2013, 5347-5359.
Spaeth, Erika L., et al., "Mesenchymal stem cell transition to tumor-associated fibroblasts contributes to fibrovascular network expansion and tumor progression", Plos ONE 4(4): e4992, 2009, 1-11.
Thijssen, Sandy, et al., "Changes in expression of fibrotic markers and histopathological alterations in kidneys of mice chronically exposed to low and high Cd doses", Toxicology, 238(2-3), 2007, 200-210.
Tsukamoto, Hidekazu, et al., "Epigenetic cell fate regulation of hepatic stellate cells", Hepatology Research, 41 (7), 2011, 675-682.
Van Midwound, et al., "A microfluidic approach for in vitro assessment of interorgan interactions in drug metabolism using intestinal and liver slices", Lap Chip, vol. 10, 2010, 2778-2786.
Vekemans, Katrien, et al., "Structural and functional aspects of the liver and liver sinusoidal cells in relation to colon carcinoma metastasis", World Journal of Gastroenterology: WJG, 11(33), 2005, 5095-5102.
Zhao, Qi, et al., "Epigenetic modifications in hepatic stellate cells contribute to liver fibrosis", The Tohoku Journal of Experimental Medicine, 229(1), 2013, 35-43.

* cited by examiner

BASIC IHC ON 2 WEEK LIVER ORGANOIDS

METHODS OF PRODUCING IN VITRO LIVER CONSTRUCTS AND USES THEREOF

CROSS REFERENCE TO RELATED APPLICATIONS

This application is a 35 U.S.C. § 371 national stage application of PCT International Application No. PCT/US2016/056942, filed on Oct. 14, 2016, which claims priority from U.S. Provisional Patent Application Ser. No. 62/241,966 filed on Oct. 15, 2015, the contents of which are incorporated herein by reference in their entireties. The above-referenced PCT International Application was published in the English language as International Publication No. WO 2017/070007 A2 on Apr. 27, 2017.

GOVERNMENT SUPPORT

This invention was made with government support under Contract No. N66001-13-C-2027 awarded by the Defense Threat Reduction Agency (DTRA) under Space and Naval Warfare Systems Center Pacific (SSC PACIFIC). The U.S. Government has certain rights to this invention.

BACKGROUND OF THE INVENTION

Many cell culture systems have traditionally relied on two-dimensional (2D) methods; however, conventional 2D systems do not reproduce intercellular and supracellular structures found in vivo. In order to model in vivo organ physiology and function, various 3D culture systems have been developed. Biologically derived matrices such as decellularized organs, artificial matrices such as synthetic polymers and hybrid of extracellular proteins and polymers, hydrogels, and inorganic substrates have been used to generate 3D scaffold structures and recapitulate in vivo organ architecture. Scientists have incorporated these bio, synthetic, and hybrid materials in fabrication methods such as weaving, electrospinning, bioprinting, micromachining, and molding. Although capable of generating useful structural complexities, these methods suffer from low reproducibility, high variability, low scalability, and difficulty in manufacturing. See generally Godoy et al., *Arch Toxicol*, 87, 1315-1530 (2013); Khetani et al., *J Lab Autom.* pii: 2211068214566939 (23 Jan. 2015); Bale et al., *Exp. Biol. Med.* 239(9), 1180-1191 (2014).

Cavnar et al., *J Lab Autom* 19(2), 208-214 (2014), describes the construction of devices and development of methods of forming 3D constructs, but does not advance the state of the art in the biological components of the 3D construct. Gunnes et al., *Toxicol. Sci.* 133(1), 67-78 (2013) describes difficulty in constructing liver organoids using a mixture of hepatocytes and non-parenchymal cells, which is circumvented via using a cell line. Kim and Rajagopalan, *PLoSOne* 5(11), e15456 (2010) describes a 3D hepatic culture where hepatocytes and endothelial cells are combined. Messner et al., *Arch Toxicol* 87, 209-213 (2013) describes the use of a hanging drop method to assemble 3D liver spheroids, but used an undisclosed mixture of hepatocytes, Kupffer cells, and endothelial (undisclosed type) cells.

SUMMARY OF THE INVENTION

According to some embodiments, cell compositions useful for making artificial liver constructs may include, in combination,: (a) hepatocyte cells, (b) Kuppfer cells, (c) hepatic stellate cells, (d) sinusoidal endothelial cells, and (e) cholangiocyte cells.

In some embodiments, (a) said hepatocyte cells may be included in an amount by number of from 70 to 90 percent; (b) said Kupffer cells may be included in an amount by number of from 5 to 20 percent; (c) said hepatic stellate cells may be included in an amount by number of from 2 to 10 percent; (d) said sinusoidal endothelial cells may be included in an amount by number of from 2 to 10 percent; and (e) said chalangiocyte cells may be included in an amount by number of from 1 to 4 percent. In some embodiments, said cells may be mammalian cells.

According to some embodiments, culture compositions may include the cell compositions described above in an aqueous culture media. In some embodiments, said culture media may further include at least one extracellular matrix (ECM) protein.

According to some embodiments, artificial liver constructs may include the cell compositions described above or the culture compositions described above. In some embodiments, said artificial liver constructs may have a diameter of 100 to 300 microns.

According to some embodiments, methods of making the artificial liver constructs described above may include performing a hanging drop culture method, a gravity-enforced self-assembly method or a method using a microfabricated mold using the culture compositions described above.

According to some embodiments, compositions may include (a) a hydrogel and (b) a plurality of artificial liver constructs described above in said hydrogel.

According to some embodiments, devices may include (a) a substrate including at least one chamber therein and (b) at least one artificial liver constructs described above in said chamber, or the compositions described above in said chamber.

According to some embodiments, methods of making a device may include (a) providing a substrate and (b) depositing at least one constructs described above or the compositions described above on said substrate. In some embodiments, said depositing step may be carried out by bioprinting, pipetting, microinjection, or microfluidic deposition.

According to some embodiments, methods of screening a compound for pharmacological and/or toxicological activity may include (a) providing the device described above, (b) administering a compound to said artificial liver construct; and then (c) detecting a pharmacological and/or toxicological response to said compound from at least one cell of said artificial liver construct.

DETAILED DESCRIPTION OF ILLUSTRATIVE EMBODIMENTS

The present invention is now described more fully hereinafter with reference to the accompanying drawings, in which example embodiments of the present invention are shown. This invention may, however, be embodied in many different forms and should not be construed as limited to the embodiments set forth herein; rather these embodiments are provided so that this disclosure will be thorough and complete and will fully convey the scope of the present invention to those skilled in the art. The disclosures of all United States patent references cited herein are to be incorporated by reference herein in their entirety.

The terminology used herein is for the purpose of describing particular embodiments only and is not intended to be limiting of the present invention. As used herein, the singular forms "a," "an" and "the" are intended to include plural forms as well, unless the context clearly indicates otherwise. It will be further understood that the terms "comprises" or "comprising," when used in this specification, specify the presence of stated features, steps, operations, elements components and/or groups or combinations thereof, but do not preclude the presence or addition of one or more other features, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

"Cells" as used herein are, in general, mammalian cells, such as dog, cat, cow, goat, horse, sheep, mouse, rabbit, rat, etc. cells. In some preferred embodiments the cells are human cells. Suitable cells are known and are commercially available, and/or may be produced in accordance with known techniques. See, e.g., U.S. Pat. No. 6,737,270.

A "media" or "culture media," as used herein, refers to an aqueous based solution that is provided for the growth, viability, or storage of cells used in carrying out the present invention. A media or culture media may be natural or artificial. A media or culture media may include a base media and may be supplemented with nutrients (e.g., salts, amino acids, vitamins, trace elements, antioxidants) to promote the desired cellular activity, such as cell viability, growth, proliferation, and/or differentiation of the cells cultured in the media. A "base media," as used herein, refers to a basal salt nutrient or an aqueous solution of salts and other elements that provide cells with water and certain bulk inorganic ions essential for normal cell metabolism and maintains intra-cellular and/or extra-cellular osmotic balance. In some embodiments, a base media may include at least one carbohydrate as an energy source and/or a buffering system to maintain the medium within the physiological pH range. Examples of commercially available base media may include, but are not limited to, phosphate buffered saline (PBS), Dulbecco's Modified Eagle's Medium (DMEM), Minimal Essential Medium (MEM), Basal Medium Eagle (BME), Roswell Park Memorial Institute Medium (RPMI) 1640, MCDB 131, Click's medium, McCoy's 5A Medium, Medium 199, William's Medium E, insect media such as Grace's medium, Ham's Nutrient mixture F-10 (Ham's F-10), Ham's F-12, α-Minimal Essential Medium (αMEM), Glasgow's Minimal Essential Medium (G-MEM) and Iscove's Modified Dulbecco's Medium. See, e.g., US Patent Application Publication No. US20150175956.

"Extracellular Matrix Proteins" (or "ECM") as used herein are known, and include but are not limited to those described in Y. Zhang et al., US Patent Application Publication No. US 20130288375, the disclosure of which is incorporated by reference herein in its entirety. See also Skardal et al., *Tissue specific synthetic ECM hydrogels for 3-D in vitro maintenance of hepatocyte function*, Biomaterials 33(18): 4565-75 (2012).

"Bioprinting" of cells, typically in a "bioink" such as a hydrogel (including but not limited to cross-linkable hydrogels) is a known technique and may be carried out in accordance with any of a variety of known methods and apparatus. See, e.g., US Patent Application Publication No. US20080194010; PCT Application Publication No. WO 2016/064648A1.

"Hanging drop" methods of culturing cells and apparatus useful therein are known and may be carried out in accordance with known techniques. See, e.g., U.S. Pat. No. 7,112,241; US Patent Application. Publication Nos. 20030235519A1; 20130040855A1; 20140179561; and 20130084634A1; and PCT Application Publication No. WO2012117083A3.

Cell compositions. A composition useful for making artificial liver constructs (or "organoids") may include, in combination: (a) hepatocyte cells, (b) Kuppfer cells, (c) hepatic stellate cells, (d) sinusoidal endothelial cells, and (e) cholangiocyte cells. In general:

(a) the hepatocyte cells are included in an amount by number of from 70 to 90 percent (most preferably 78 percent);
(b) the Kupffer cells are included in an amount by number of from 5 to 20 percent (most preferably 10 percent);
(c) the hepatic stellate cells are included in an amount by number of from 2 to 10 percent (most preferably 5 percent);
(d) the sinusoidal endothelial cells are included in an amount by number of from 2 to 10 percent (most preferably 5 percent); and
(e) the chalangiocyte cells are included in an amount by number of from 1 to 4 percent (most preferably 2 percent).

Culture compositions. The cell compositions may be combined in an organ-forming culture media (e.g., aqueous organ-forming culture media) to provide a culture composition. In preferred embodiments, the culture media may further include at least one extracellular matrix (ECM) protein (e.g., laminin, collagen type I, collagen type IV, fibronectin, elastin, or a combination thereof). Preferably, the at least one ECM protein may include at least collegen type I. The ECM protein(s) may be included in any suitable amount, typically from 10 nanograms per milliliter to 1 milligram per milliliter (preferably 1 to 10 micrograms per milliliter). In some embodiments, the organ-forming culture media may include from 10 to 30 percent (most preferably 20 percent) by weight of serum (e.g., heat inactivated fetal bovine serum).

Artificial liver constructs. An artificial liver construct that may include or may be produced from a cell composition as described herein may be produced by any suitable technique, such as by hanging drop culture. In some embodiments, the artificial liver construct may have a diameter of 100 or 200 to 250 or 300 microns. In some embodiments, the total number of all cells in the artificial liver construct may be from 100 or 1,000 to 2,000 or 10,000 (preferably about 1,500 or 1,000 cells per organoid). In some embodiments, the artificial liver construct may be characterized by (i) the presence of at least one, two, or all three of hepatocyte microvilli, bile canaliculus like structures, and/or lysosomes; and/or (ii) the expression of at least one, two or all three of urea, albumin, and/or alpha 1-antitrypsin for a time of at least 10, 20, or 30 days when maintained in culture.

Methods of making artificial liver constructs. In some embodiments, artificial liver constructs may be made by using spheroid culture methods (i.e., scaffold-free aggregate culture methods). The spheroid culture methods may be useful for co-culture, in which cells may organize themselves into distinct layers. Specifically, hanging drop culture methods may be used to make self-assembled cellular aggregate structures representing artificial liver constructs. Hanging drop culture methods may include depositing droplets including the culture composition onto a culture substrate (e.g., a hanging drop plate) and then culturing the cells in the culture composition. In some embodiment, the hanging drop culture methods may optionally include turning the culture substrate over before culturing the cells. Hanging drop culture methods allow the cells to form an aggregate in the bottom of a droplet hanging from a surface of the substrate. Foty, Ramsey, *A Simple Hanging Drop Cell Culture Protocol for Generation of 3D Spheroids*, Journal of Visualized Experiments: JoVE, no. 51. doi:10.3791/2720 (2011). Hanging drop culture methods may be able to produce uniform sizes of tissue based on the number of cells seeded in the drop. See, e.g., Mehta et al., *Opportunities and Challenges for Use of Tumor Spheroids as Models to Test Drug Delivery and Efficacy*, Journal of Controlled Release 164 (2): 192-204 (2012). Commercial hanging drop plates from InSphero (Schlieren, Switzerlan) and 3D Biomatrix (Ann Arbor, Mich., USA) may be used to generate artificial liver constructs. However, any methods that facilitate close cell-cell contacts in the absence of interacting substrates may be used, such as gravity-enforced self-assembly methods (See, e.g., Kelm et al., Trends Biotechnol. 2004, 22:195-202) or methods using microfabricated molds (See, e.g., Yeon et al., PLos One 2013, 8(9), e73345).

In some embodiments, functional additives may be added into the culture composition to form artificial liver constructs. A small amount of a protein derived from extracellular matrix (ECM), such as laminin, collagen I or IV, fibronectin, or elastin, may be added to the culture composition. In some embodiments, a protein derived from liver extracellular matrix (ECM) may be added to the culture composition. The preferred composition and concentration of the cell-binding protein is collagen at 1-10 ug/mL (e.g., collagen type I). In addition, in some embodiments, the culture composition has a high fraction of serum (e.g., inactivated fetal bovine serum) at >10%, preferably at 20%.

Hydrogel compositions. The artificial liver constructs or organoids described above can be used per se, or combined with a hydrogel, such as a cross-linkable hydrogel, for further use. Suitable hydrogels are known and may include, but are not limited to, those described in Skardal et al., *A hydrogel bioink toolkit for mimicking native tissue biochemical and mechanical properties in bioprinted tissue constructs,* Acta Biomater. 25: 24-34 (2015).

Hydrogels fall into two main categories: naturally-derived hydrogels and synthetic hydrogels. Naturally-derived hydrogels and synthetic hydrogels may be mixed to form hybrid hydrogels. Naturally-derived hydrogels may include Matrigel®, which is made out of native extracellular matrix proteins collected from a cell line, as well as collagen and alginate. Naturally-derived hydrogels may use decellularized tissue extracts. Extracellular matrix may be collected from a specific tissue and may be combined with a hydrogel material to be used to support cells of that tissue type. See, e.g., Skardal et al., *Tissue Specific Synthetic ECM Hydrogels for 3-D in vitro Maintenance of Hepatocyte Function,* Biomaterials 33 (18): 4565-75 (2012). Chitosan hydrogel is an example of a naturally-derived hydrogel that is degradable and supportive for several different cell types. See, e.g., Moura et al., *In Situ Forming Chitosan Hydrogels Prepared via Ionic/Covalent Co-Cross-Linking,* Biomacromolecules 12 (9): 3275-84 (2011). Hyaluronic acid hydrogels may also be used. See, e.g., Skardal et al., *A hydrogel bioink toolkit for mimicking native tissue biochemical and mechanical properties in bioprinted tissue constructs,* Acta Biomater. 25: 24-34 (2015).

Synthetic hydrogels may be produced from a variety of materials (e.g., Poly-(ethylene glycol)) and using many techniques. In contrast to naturally-derived hydrogels, synthetic hydrogels may be produced uniformly and may be easily reproducible and characterized. Synthetic hydrogels may, however, lack some functional signals for cells, like the active sites found in natural extracellular matrix, limiting their potential to support cells. See, e.g., Mahoney et al., *Three-Dimensional Growth and Function of Neural Tissue in Degradable Polyethylene Glycol Hydrogels,* Biomaterials 27 (10): 2265-74 (2006). Hybrid hydrogels may offer a compromise and may allow for more control over the ability to reconstruct a specific microenvironment. By combining natural components, such as extracellular matrix molecules (e.g., extracellular matrix proteins), with defined synthetic hydrogels, a more easily reproducible and functional hydrogels can be produced. See, e.g., Salinas et al., *Chondrogenic Differentiation Potential of Human Mesenchymal Stem Cells Photoencapsulated within Poly(Ethylene Glycol)-Arginine-Glycine-Aspartic Acid-Serine Thiol-Methacrylate Mixed-Mode Networks*, Tissue Engineering 13 (5): 1025-34 (2007).

Bioprinting of artificial liver constructs. In some embodiments, the artificial liver constructs described above can be combined with a hydrogel (e.g., biocompatible hydrogels) by using bioprinting techniques. In some embodiments, the hydrogel may be an extrudable hydrogel composition (or "bioink"). The hydrogel composition may include a cross-linkable prepolymer and a post-deposition crosslinking group. The cross-linkable prepolymer may include acrylate-based crosslinkers (e.g., polyethylene (glycol) diacrylate (PEGDA)) and the post-deposition crosslinking group may include alkyne-based crosslinkers (e.g., polyethylene glycol (PEG) alkyne, polyethylene glycol (PEG) 8-Arm alkyne). The hydrogel composition may also include thiolated hyaluronic acid (HA), thiolated gelatin, and unmodified HA, gelatin and/or extracellular matrix (ECM) material (e.g., liver ECM materials).

The hydrogel composition may be prepared and spontaneously crosslink through thiol-acrylate binding, resulting in a soft, extrudable material. Bioprinting may be performed by depositing the extrudable hydrogel composition. In some embodiments, the hydrogel composition, prior to deposition, may have a stiffness of from 0.05, 0.1 or 0.5 to 1, 5 or 10 kiloPascals (kPa), or more, at room temperature and atmospheric pressure. The bioprinted structures may be brought to the target stiffness by cross-linking the cross-linkable prepolymer with the post-deposition crosslinking group by an amount sufficient to increase the stiffness of the hydrogel composition. In some embodiments, the cross-linking step may increase the stiffness of the hydrogel composition from 1 or 5 to 10, 20 or 50 kiloPascals (kPa), or more, at room temperature and atmospheric pressure. The cross-linking step may be performed by, for example, heating the hydrogel composition, irradiating the hydrogel composition with light (e.g., ambient light, UV light), and/or altering the pH of the hydrogel composition.

Devices. Devices useful for in vitro compound screening with artificial liver constructs or organoids of the present invention typically are produced by (a) providing a substrate or device body (e.g., a microfluidic device) having at least one chamber formed therein (the chamber preferably include an inlet and outlet opening formed therein); and (b) depositing at least one construct as described above (per se, or as a composition thereof in combination with a hydrogel) in the chamber. The depositing step may be carried out by any suitable technique, such as bioprinting, pipetting, microinjection, microfluidic deposition, etc. The device may be provided in the form of a cartridge for "plug in" or insertion into a larger apparatus including pumps, culture media reservoir(s), detectors, and the like.

The device body or microfluidic device may itself be formed of any suitable material or combination of materials. Examples include, but are not limited to, polydimethylsiloxane (PDMS), polystyrene, polymethyl methacrylate (PMMA), polyacrylamide, polyethylene glycol (PEG) including functionalized PEG (e.g. PEG diacrylate, PEG diacrylamide, PEG dimethacrylate, etc., or any of the foregoing PEGs in multi-arm forms, etc.), natural polymers or proteins that can be cross-linked or cured (e.g., hyaluronic acid, gelatin, chondroitin sulfate, alginate, etc., including derivatives thereof that are functionalized with chemical groups to support cross linking, and combinations thereof).

The device body may be formed by any suitable process, including molding, casting, additive manufacturing (3D printing), lithography, etc., including combinations thereof.

Storing and shipping of devices. Once produced, devices as described above in cartridge form may be used immediately, or prepared for storage and/or transport.

To store and transport the product, a transient protective support media that is a flowable liquid at room temperature (e.g., 25° C.), but gels or solidifies at refrigerated temperatures (e.g., 4° C.), such as a gelatin mixed with water, may be added into the device to substantially or completely fill the chamber(s), and preferably also any associated conduits. Any inlet and outlet ports may be capped with a suitable capping element (e.g., a plug) or capping material (e.g., wax). The device may be then packaged together with a cooling element (e.g., ice, dry ice, a thermoelectric chiller, etc.) and all may be placed in a (preferably insulated) package.

In some embodiments, to store and transport the product, a transient protective support media that is a flowable liquid at cooled temperature (e.g., 4° C.), but gels or solidifies at warm temperatures such as room temperature (e.g., 20° C.) or body temperature (e.g., 37° C.), such as poly(N-isopropylacrylamide) and poly(ethylene glycol) block co-polymers, may be added into the device to substantially or completely fill the chamber(s), and preferably also any associated conduits.

Upon receipt, the end user may simply remove the device from the associated package and cooling element, may allow the temperature to rise or fall (depending on the choice of transient protective support media), may uncap any ports, and may remove the transient protective support media with a syringe (e.g., by flushing with growth media).

Methods of use of devices. Devices described above can be used for in vitro screening (including high through-put screening) of a compound (or compounds) for pharmacological and/or toxicological activity. Such screening can be carried out by: (a) providing a device as described above; (b) administering a compound to the artificial liver construct (e.g., by adding to a growth media being flowed through the chamber containing the construct); and then (c) detecting a pharmacological and/or toxicological response to the compound from at least one cell of the construct. Detecting of the response may be carried out by any suitable technique, including microscopy, histology, immunoassay, etc., including combinations thereof, depending on the particular response, or set of responses, being detected. Such response or responses may be cell death (including senescence and apoptosis), cell growth (e.g., benign and metastatic cell growth), absorption, distribution, metabolism, or excretion (ADME) of the compound, or a physiological response (e.g., upregulation or downregulation of production of a compound by the at least one cell), or any other biological response relevant to pharmacological and/or toxicological activity.

The present invention is explained in greater detail in the following non-limiting Examples.

EXAMPLES

A. Materials.

Source of cells. Hepatocytes/cholangiocytes were obtained from Triangle Research Labs (6 Davis Drive, Research Triangle Park, N.C. USA 27709) as Product No. HUCP16. Kuppfer cells were obtained from Life Technologies/ThermoFisher Scientific (81 Wyman Street, Waltham, Mass. USA 02451) as Product No. HUKCCS. Hepatic Stellate cells were obtained from ScienCell (6076 Corte Del Cedro, Carlsbad, Calif. USA 92011) as Product No. HHSteC/3830. Liver sinusoidal endothelial cells were obtained from ScienCell as Product No. HHSEC/5000.

Organ Formation Media. Complete Hepatocyte culture medium (Lonza) containing 20% heat inactivated fetal bovine serum and 1 Ougiml rat tail collagen type I. The media is formulated as follows: To 500 ml of Lonza Hepatocyte Basal Culture Medium (product CC3197) are added single-quot supplements (product #CC4182) Ascorbic acid, bovine serum albumin (fatty acid free), human epidermal growth factor, transferrin, insulin and gentamycin in the quantities specified by the manufacturer. Hydrocortisone supplement is omitted to enhance the inflammatory response. To this media is added 20% heat inactivated premium select fetal bovine serum (Atlanta Biologicals product # S11550H) and 10 ug/ml sterile rat tail collagen type I (Life technologies product #A1048301).

3D Construct Maintenance Media. This media consists of Complete Hepatocyte Culture media as formulated above but without fetal bovine serum or rat tail collagen.

B. Methods.

Liver organ constructs are generated from a mixture of hepatocytes, Kupffer cells, hepatic stellate cells, cholangiocytes, and sinusoidal endothelial cells. Although mixtures of liver cells have been used previously, this composition of the mixture provides a longer duration of performance and higher performance. The number of cells and dimension of organ structures also better represent in vivo structures and functions. Specifically, ranges of a total number of cells used are 100-10,000, optimal being approximately 1,000 or 1,500. One preferred composition of the cell mixture by number of is 78%:10%:5%:5%:2% for hepatocytes, Kupffer cells, hepatic stellate cells, sinusoidal endothelial cells, and cholangiocytes, respectively.

Hanging drop methods have been employed to generate self-assembled cellular aggregate structures representing micro liver structure. A significant part of the present disclosure is a technical method that enables the formation of liver cellular aggregates. Unlike many cell lines and tumor cells, the cell mixture disclosed herein does not readily form an aggregate structure if it is simply mixed in a culture media and dispensed into hanging drops. The present disclosure includes conditions and functional additives for this mixture of cells to form 3D structures. A small amount of a protein derived from extracellular matrix (ECM), such as laminin, collagen I or IV, fibronectin, or elastin, is added to the cell mixture. The preferred composition and concentration of the cell-binding protein is collagen at 1-10 ug/mL (e.g., collagen type I). In addition, the cell mixture has a high fraction of serum, preferably inactivated fetal bovine serum at >10%, preferably at 20%.

After approximately 3 days in culture, the mixture of cells transforms into a 3D construct, approximately 200-250 micron in diameter. Once formed, the 3D liver construct may be sustained in a conventional hepatocyte maintenance media, with or without serum. The 3D liver constructs have demonstrated remarkably long duration of viability and function, highly relevant physiological function such as CYP activity, inflammatory responses, and liver-specific biomarker production. Production of albumin, urea, and alpha-1 antitrypsin indicate stable long term culture of the 3D constructs (see below). Activity of exemplary cytochrome 450 isozymes 3A4 and 2C19 demonstrate sustained activity >4 weeks. In addition, the liver organ construct is capable for responding to an inflammatory stimulus, such as lipopolysaccharide (LPS), as shown below.

Once formed, the constructs are incorporated into a biocompatible hydrogel, in which the 3D liver constructs are suspended. The composition of hydrogel has been developed to maintain the 3D structure of the liver constructs. Conventional ECM-derived or synthetic hydro gels are incapable of maintaining the structure of the liver constructs and sustaining biological activities. Two-components of polyethylene glycol diacrylate (PEGDA) and polyethylene-alkyne as described in Skardal et al., Acta Biomater. 25, 24-34 (2015) were used to generate hydrogels that have Young's modulus between 40-100 Pa. As the 3D liver constructs can be suspended in a hydrogel, bioprinting is possible. Bioprinting provides control over spatial arrangement of the organ constructs within assay devices and apparatus.

C. Results.

Figure 1:
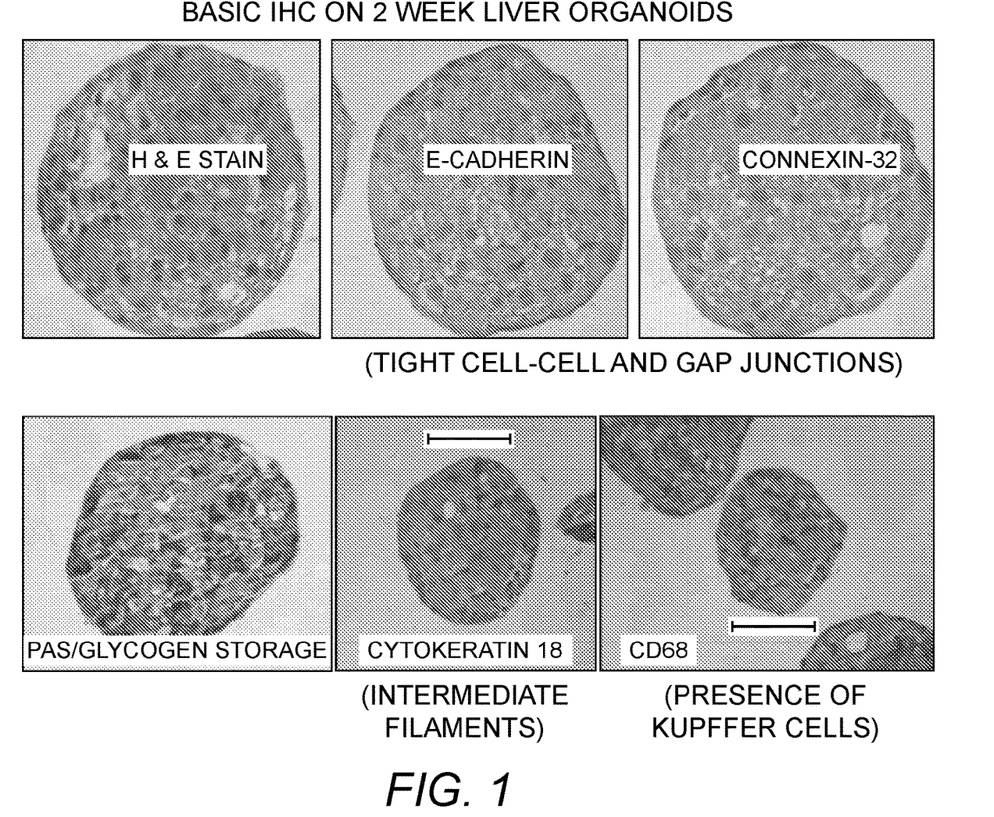
FIG. 1 shows basic immunohistochemistry staining results for 2 week old liver constructs of embodiments of the present invention.
Figure 2A:
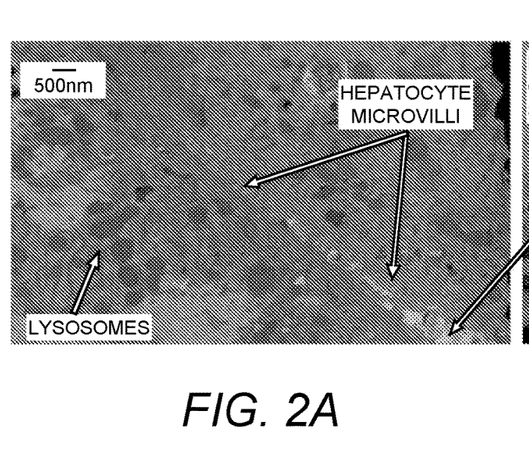
FIGS. 2A-2B show electron microscope images of newly formed liver constructs of embodiments of the present invention.
Figure 2B:
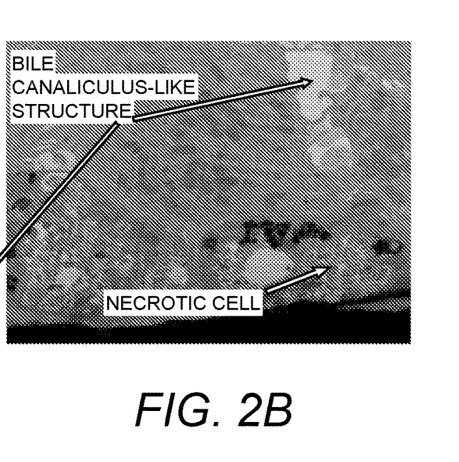
Figure 3:
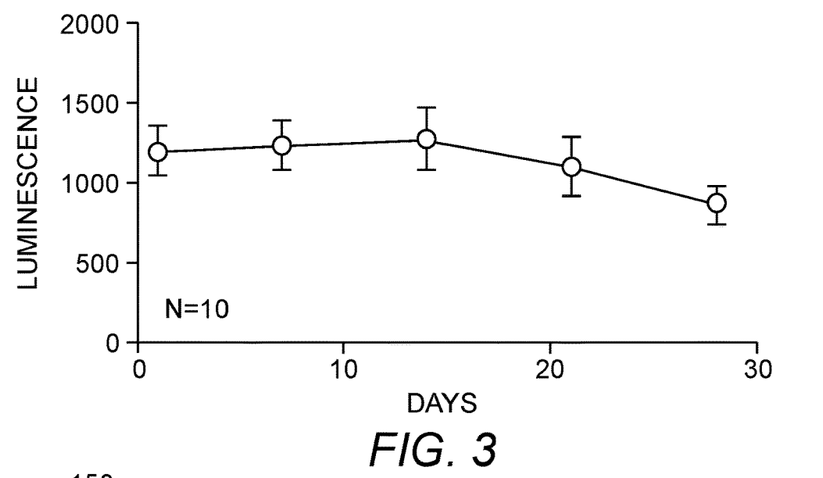
FIG. 3 illustrates the long term viability of liver constructs of embodiments of the present invention as demonstrated by CellTiter-Glo ATP assay.

Basic immunohistochemistry staining results for 2 week old liver constructs is given in FIG. 1. Electron Microscope images of newly-formed liver constructs are given in FIGS. 2A-2B. Long term-viability of liver constructs is demonstrated by CellTiter-Glo ATP assay in FIG. 3.

Figure 4:
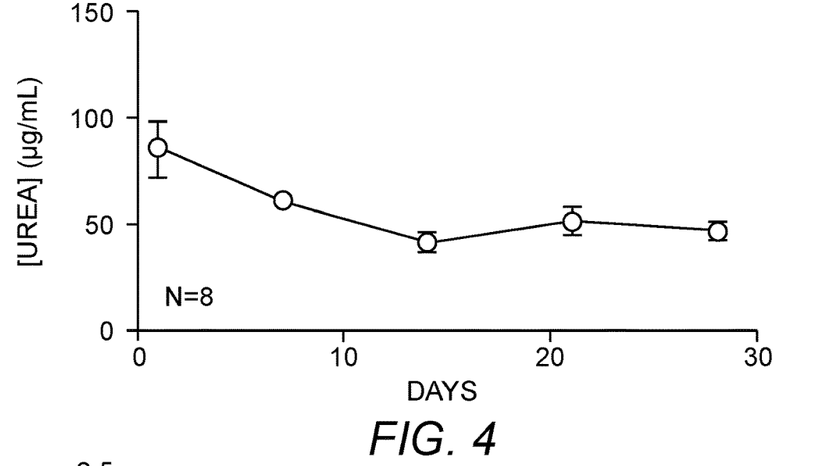
FIG. 4 shows long term production of the liver biomarker urea by liver constructs of embodiments of the present invention.
Figure 5:
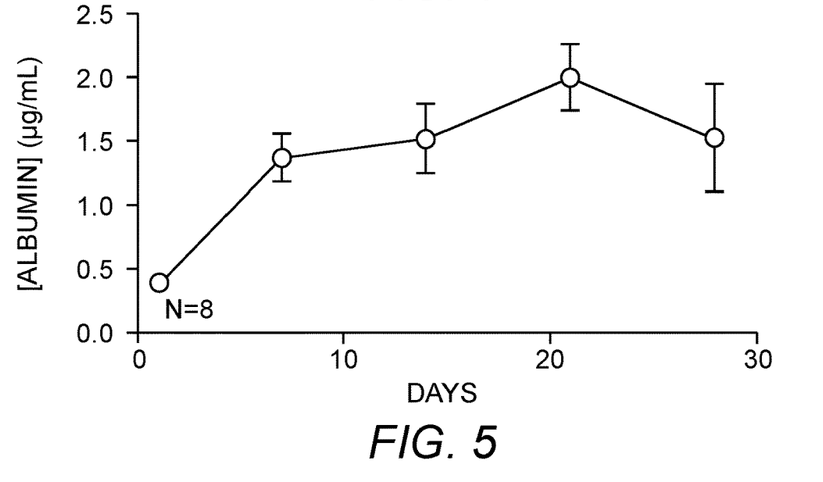
FIG. 5 shows long term production of the liver biomarker albumin by liver constructs of embodiments of the present invention.
Figure 6:
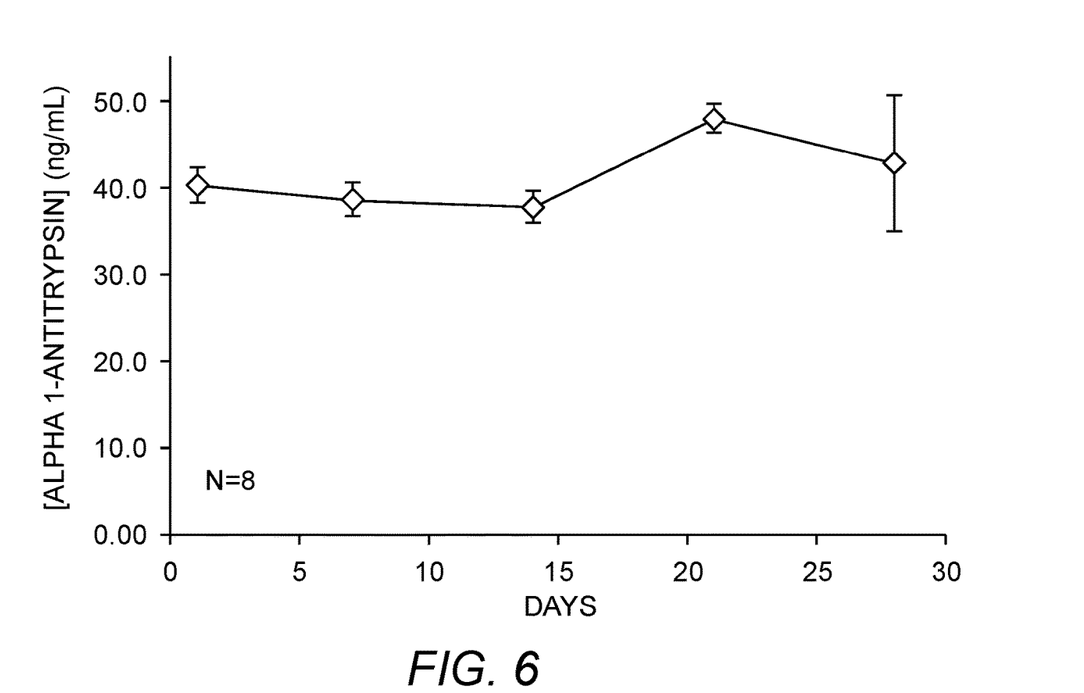
FIG. 6 shows long term production of the liver biomarker alpha-1-antitrypsin by liver constructs of embodiments of the present invention.

FIG. 4 shows long term production of the liver biomarker urea by artificial liver constructs. FIG. 5 shows long term production of the liver biomarker albumin by artificial liver constructs. FIG. 6 shows long term production of the liver biomarker alpha-1-antitrypsin by artificial liver constructs.

Figure 7:
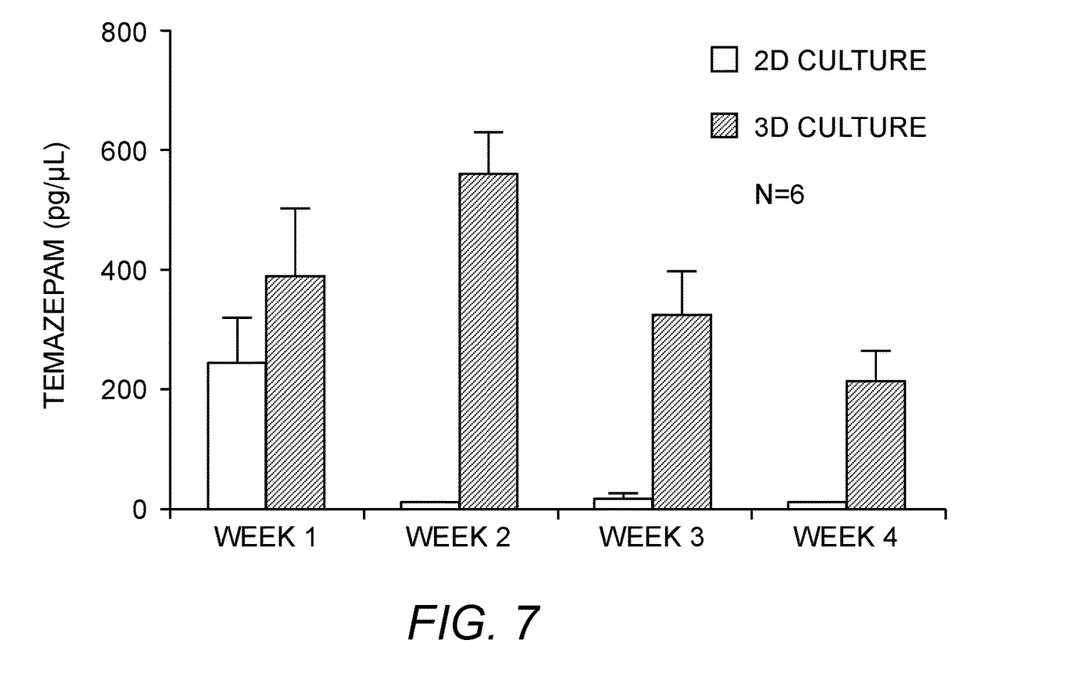
FIG. 7 shows the long term metabolism of diazepam to temazepam by 3D liver constructs of embodiments of the present invention, as compared to 2D cultures.
Figure 8:
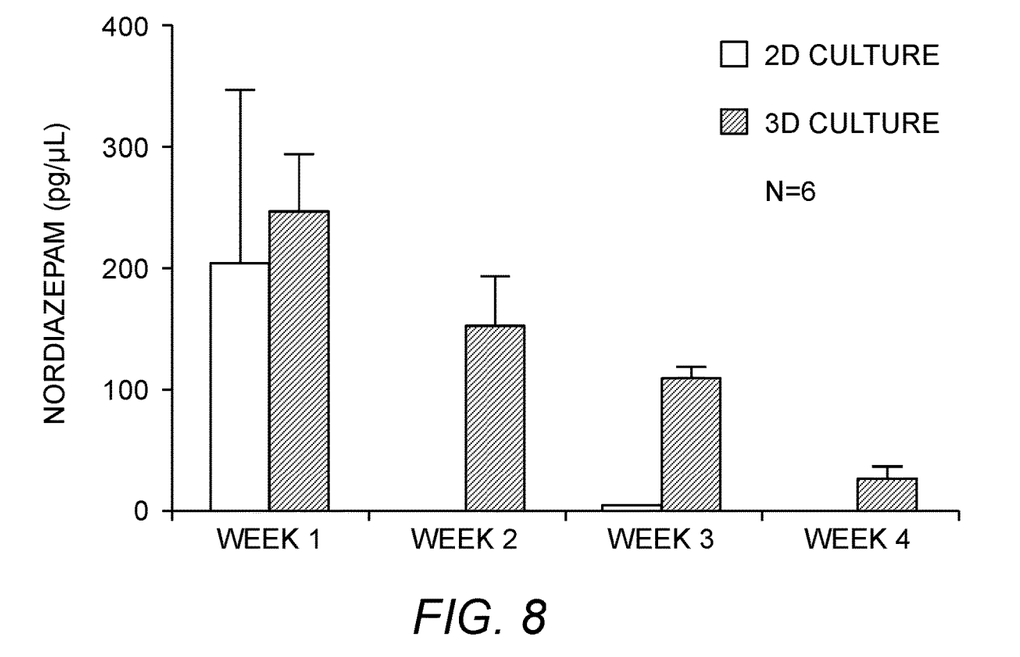
FIG. 8 shows the long term metabolism of diazepam to nordiazepam by 3D liver constructs of embodiments of the present invention, as compared to 2d cultures.

FIG. 7 shows the long term metabolism of diazepam to temazepam by 3D liver constructs, as compared to 2D cultures. FIG. 8 shows the long term metabolism of diazepam to nordiazepam by 3D liver constructs, as compared to 2D cultures.

Figure 9:
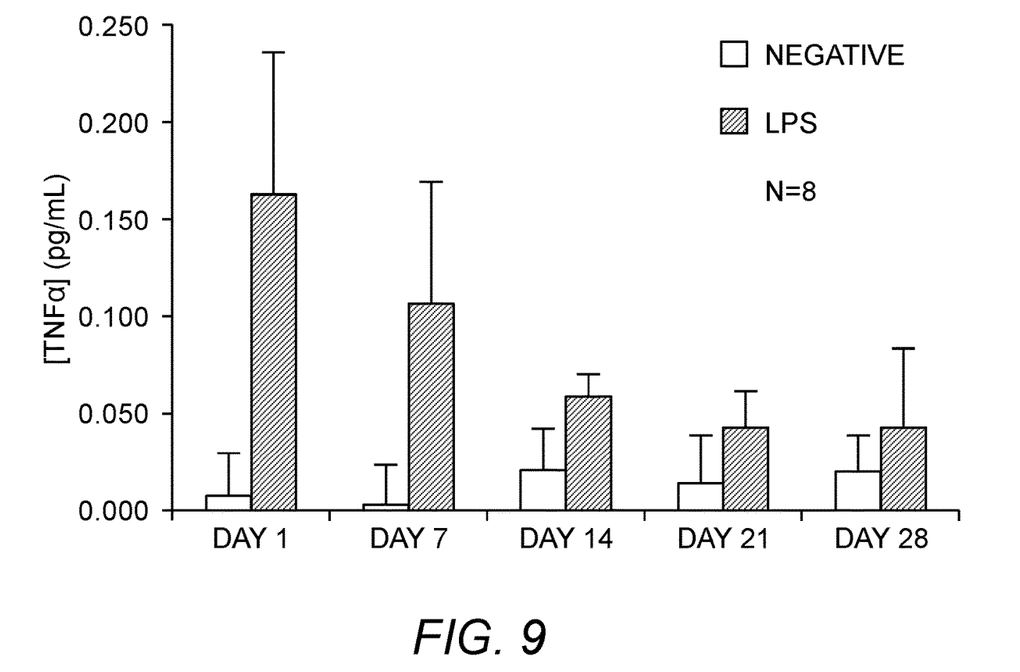
FIG. 9 shows the long term inflammatory response of liver constructs of embodiments of the present invention to lipopolysaccharide (LPS).

FIG. 9 shows the long term inflammatory response of liver constructs to lipopolysaccharide (LPS).

Figure 10:
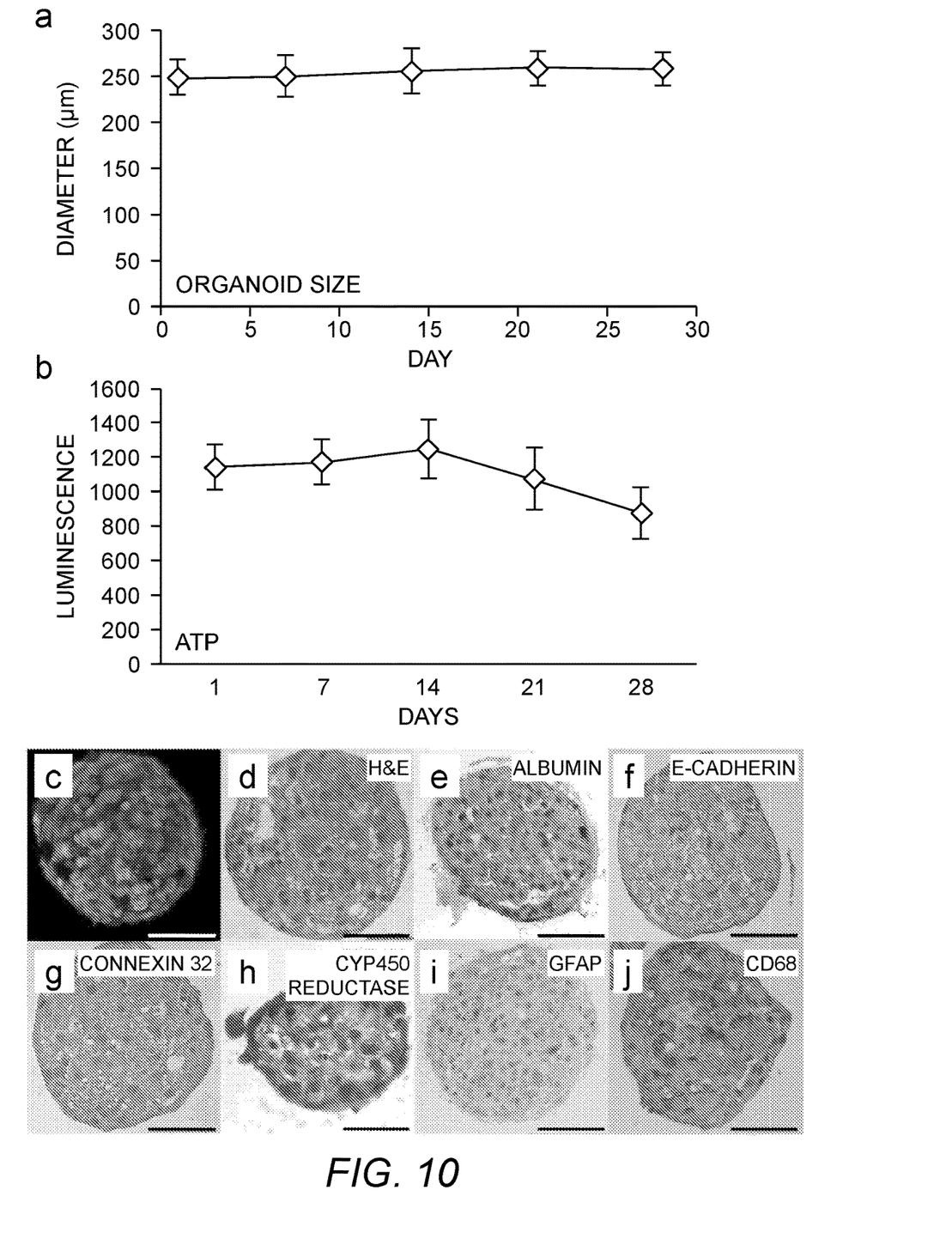
FIGS. 10a and 10b illustrate the long term stability and viability of liver constructs of embodiments of the present invention.
FIG. 10c shows LIVE/DEAD staining result for liver constructs of embodiments of the present invention.
FIGS. 10d-10j show histological and immunohistochemical staining results for liver constructs of embodiments of the present invention.

FIGS. 10a and 10b illustrate the long term stability and viability of liver constructs of embodiments of the present invention, FIG. 10c shows LIVE/DEAD staining result for liver constructs of embodiments of the present invention, and FIGS. 10d-10j show histological and immunohistochemical staining results for liver constructs of embodiments of the present invention. FIG. 10a. Average organoid diameter remains consistent over 28 days. FIG. 10b. Liver organoids remain metabolically active over 28 days, as determined by luminescence readings of ATPase. FIG. 10c. LIVE/DEAD staining (shown at 14 days) shows high cell viability in the organoids. Green—calcein AM-stained viable cells; Red—ethidium homodimer-1-stained dead cells; Diameter 261 μm. FIGS. 10d-10j. Histological and immunohistochemical staining depict organoid structure and organization. FIG. 10d. H&E staining shows overall organoid morphology. Primary human hepatocytes are identified by albumin expression (FIG. 10e), and exhibit epithelial organization shown through E-cadherin expression (FIG. 10f) around the cell membrane, and also express connexin 32 (FIG. 10g) and cytochrome P450 reductase (FIG. 10h). Hepatic Stellate and Kupffer cells are identified by GFAP (FIG. 10i), and CD68 (FIG. 10j), respectively. Purple—hemotoxylin-stained nuclei; Pink—cell cytoplasm; Brown—indicated stain; Scale bar—100 μm.

FIGS. 11a-11e show the long term baseline liver function and metabolism of 3D liver constructs of embodiments of the present invention, as compared to 2D cultures. Normalized urea (FIG. 11a) and albumin (FIG. 11b) secretion into media, analyzed by ELISA and colorimetric assays show dramatically increased functional output in the 3-D organoid format in comparison to 2-D hepatocyte sandwich cultures. Quantification of the diazepam metabolites temazepam (FIG. 11c), noridazepam (FIG. 11d), and oxazepam (FIG.

Figure 11:
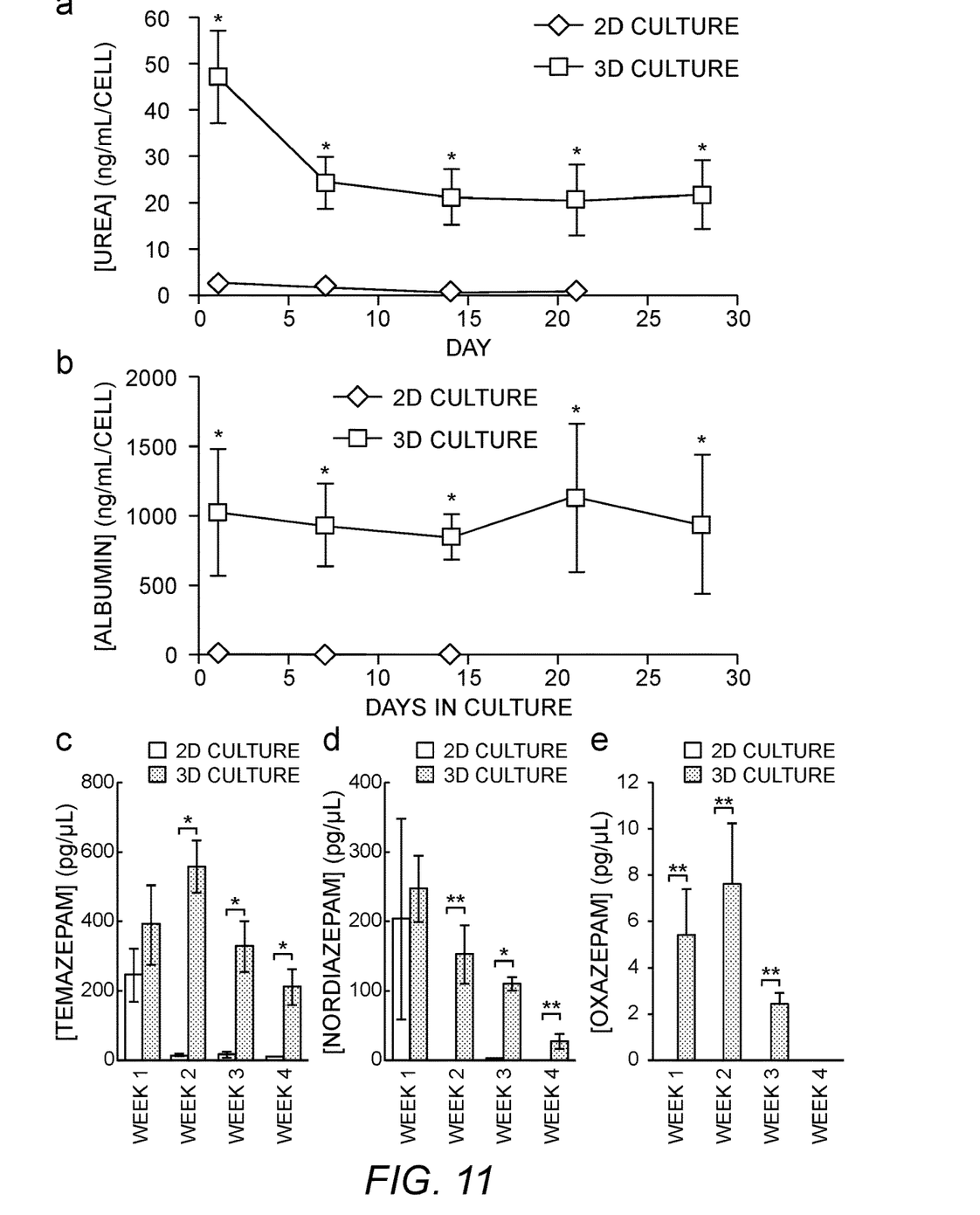
FIGS. 11a-11e show the long term baseline liver function and metabolism of 3D liver constructs of embodiments of the present invention, as compared to 2D cultures.

11e) primarily by CYP2C19 and CYP3A4. Statistical significance: *p <0.05 between 3-D and 2-D comparisons at each time point.

Figure 12:
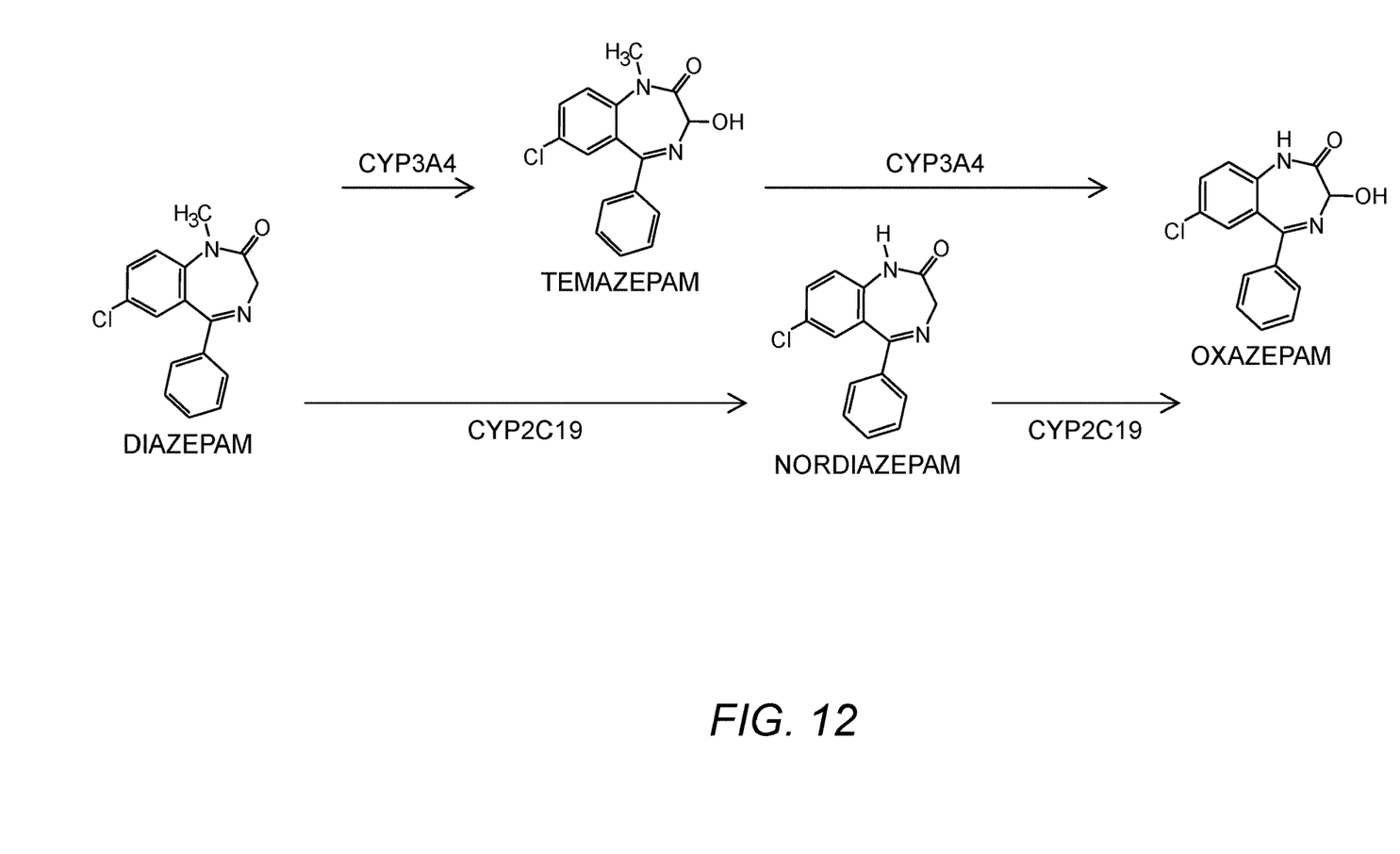
FIG. 12 illustrates liver construct metabolism of diazepam.

FIG. 12 illustrates liver construct metabolism of diazepam into temazepam, nordiazepam, and oxazepan by cytochrome p450 isoforms.

The foregoing is illustrative of the present invention and is not to be taken as limiting thereof. The present invention is defined by the following claims, with equivalents of the claims to be included therein.

That which is claimed is:

1. An artificial liver construct comprising:
a cell composition, the cell composition comprising, in combination:
(a) hepatocyte cells in an amount by number of from 70 to 90 percent;
(b) Kupffer cells in an amount by number of from 5 to 20 percent;
(c) hepatic stellate cells in an amount by number of from 2 to 10 percent;
(d) sinusoidal endothelial cells in an amount by number of from 2 to 10 percent; and
(e) cholangiocyte cells in an amount by number of from 1 to 4 percent.

2. The artificial liver construct of claim 1, wherein said hepatocyte cells, said Kupffer cells, said hepatic stellate cells, and said cholangiocyte cells are mammalian cells.

3. The artificial liver construct of claim 1 further comprising a single aqueous culture medium that comprises the cell composition, wherein said aqueous culture medium further comprises at least one extracellular matrix (ECM) protein.

4. The artificial liver construct of claim 3, wherein said at least one ECM protein comprises collagen type I.

5. The artificial liver construct of claim 3, wherein said at least one ECM protein is included in an amount of from 10 nanograms per milliliter to 1 milligram per milliliter.

6. The artificial liver construct of claim 3, wherein said aqueous culture medium further comprises from 10 to 30 percent by weight of serum.

7. The artificial liver construct of claim 1, wherein said artificial liver construct has a diameter of 100 to 300 microns.

8. The artificial liver construct of claim 1, wherein a total number of all cells in said artificial liver construct is from 100 to 10,000.

9. The artificial liver construct of claim 1, wherein said artificial liver construct is characterized by
(i) the presence of at least one, two, or all three of hepatocyte microvilli, bile canaliculus like structures, and/or lysosomes; and/or
(ii) the expression of at least one, two or all three of urea, albumin, and/or alpha 1-antitrypsin for a time of at least 10 days when maintained in culture.

10. The artificial liver construct of claim 1, wherein said artificial liver construct is in an aggregate form.

11. A method of making the artificial liver construct of claim 1, the method comprising performing a hanging drop culture method, a gravity-enforced self-assembly method or a method using a microfabricated mold using a culture composition,
wherein the culture composition comprises a cell composition comprising, in combination: (a) hepatocyte cells, (b) Kupffer cells, (c) hepatic stellate cells, (d) sinusoidal endothelial cells, and (e) cholangiocyte cells,
wherein the cell composition is in an aqueous culture medium, and
wherein said aqueous culture medium further comprises at least one extracellular matrix (ECM) protein.

12. The method of claim 11, wherein performing the hanging drop culture method comprises:
depositing droplets comprising the culture composition onto a culturing substrate; and then
culturing the hepatocyte cells, the Kupffer cells, the hepatic stellate cells, and the cholangiocyte cells in the culture composition.

13. A composition comprising:
(a) a hydrogel; and
(b) a plurality of artificial liver constructs of claim 1 in said hydrogel.

14. A device comprising
(a) a substrate comprising at least one chamber therein; and
(b) at least one artificial liver construct of claim 1 in said chamber.

15. The device of claim 14, wherein the device is packaged in a container with a transient protective support medium in said chamber in a gelled form, and optionally together with a cooling element in said container.

16. A method of making a device, the method comprising:
(a) providing a substrate; and
(b) depositing at least one artificial liver construct of claim 1 onto the substrate.

17. The method of claim 16, wherein said depositing step is carried out by bioprinting, pipetting, microinjection, or microfluidic deposition.

18. The method of claim 16, wherein said depositing step is carried out by bioprinting a composition on said substrate, wherein the composition comprises a hydrogel and a plurality of artificial liver constructs,
wherein one of the plurality of artificial liver constructs comprises a cell composition comprising, in combination: (a) hepatocyte cells, (b) Kupffer cells, (c) hepatic stellate cells, (d) sinusoidal endothelial cells, and (e) cholangiocyte cells, and
wherein said hydrogel comprises a cross-linkable prepolymer that is configured to crosslink spontaneously before said depositing step and a post-deposition crosslinking group that is configured to crosslink with said cross-linkable prepolymer after said depositing step.

19. The method of claim 18, further comprising performing a cross-linking step to crosslink said post-deposition crosslinking group with said cross-linkable prepolymer by irradiating said hydrogel with light.

20. The method of claim 18, wherein the cross-linkable prepolymer comprises polyethylene (glycol) diacrylate (PEGDA), and wherein the post-deposition crosslinking group comprises polyethylene glycol (PEG) alkyne.

21. A method of screening a compound for pharmacological and/or toxicological activity, the method comprising:
(a) providing the device of claim 16,
(b) administering a compound to said artificial liver construct; and then
(c) detecting a pharmacological and/or toxicological response to said compound from at least one cell of said artificial liver construct.

22. The method of claim 21, wherein said response comprises cell death, cell growth, absorption, distribution, metabolism, or excretion of said compound, or a physiological response.

23. The artificial liver construct of claim 10, wherein said artificial liver construct is a three-dimensional liver spheroid.

24. The artificial liver construct of claim 1, wherein the cell composition comprises, in combination:
   (a) hepatocyte cells in an amount by number of 78 percent;
   (b) Kupffer cells in an amount by number of 10 percent;
   (c) hepatic stellate cells in an amount by number of 5 percent;
   (d) sinusoidal endothelial cells in an amount by number of 5 percent; and
   (e) cholangiocyte cells in an amount by number of 2 percent.

* * * * *

UNITED STATES PATENT AND TRADEMARK OFFICE
CERTIFICATE OF CORRECTION

PATENT NO. : 11,732,241 B2
APPLICATION NO. : 15/768293
DATED : August 22, 2023
INVENTOR(S) : Atala et al.

It is certified that error appears in the above-identified patent and that said Letters Patent is hereby corrected as shown below:

In the Specification

Column 9, Line 7: Please correct "1 Ougiml rat" to read --10ug/ml rat--

Signed and Sealed this
Seventh Day of November, 2023

Katherine Kelly Vidal
*Director of the United States Patent and Trademark Office*